United States Patent [19]

Tobe et al.

[11] Patent Number: 5,604,263
[45] Date of Patent: Feb. 18, 1997

[54] TREATING OSTEOPOROSIS WITH HUMULONES

[75] Inventors: Hiroyasu Tobe, Kanagawa; Kazuyuki Kitamura, Saitama, both of Japan

[73] Assignee: Hoechst Japan Limited, Tokyo, Japan

[21] Appl. No.: 420,728

[22] Filed: Apr. 10, 1995

[30] Foreign Application Priority Data

Apr. 12, 1994 [JP] Japan .................................. 6-073230

[51] Int. Cl.$^6$ .................................................. A61K 31/12
[52] U.S. Cl. ............................................................ 514/690
[58] Field of Search ............................................... 514/690

[56] References Cited

U.S. PATENT DOCUMENTS

| 3,892,808 | 7/1975 | Mitchell | 260/586 D |
| 5,370,863 | 12/1994 | Barney et al. | 424/49 |

FOREIGN PATENT DOCUMENTS

| 0606599A1 | 7/1994 | European Pat. Off. . |
| 1901277 | 8/1970 | Germany . |

OTHER PUBLICATIONS

Yoshikawa et al., "Roles of Osteoblasts in Bone Remodeling," Journal of Clinical and Experimental Medicine 165 (9):568–71 (1993) (with English translation).

Mizobuchi et al., "Antifungal Activities of Hop Bitter Resins and Related Compounds," Agric. Biol Chem. 49(2):399–403 (1985).

Anteunis et al., "The Complex of Humulone and 1,2–Diaminobenzene," Bull. Soc. Chim. Belg. 72:60–68 (1963).

Obara et al., "A Synthetic Route to (+/–)–Humulone," Bull. Chem. Soc. Jpn. 62(9):3034–35 (1989).

Alderweireldt et al., "Nuclear Magnetic Resonance Spectroscopy and the Analysis of the Alpha Acids of Hops," Wallerstein Communications 27(92):19–28 (1964).

Tagashira Motoyuki "Utilization of Humulones Having Antioxidant Action," Patent Abstracts of Japan vol. 94, No. 011 and JP–A–06 312924 (Asahi Breweries Ltd.) (Aug. 11, 1994).

*Primary Examiner*—Theodore J. Criares
*Attorney, Agent, or Firm*—Finnegan, Henderson, Farabow, Garrett & Dunner, L.L.P.

[57] ABSTRACT

A pharmaceutical composition for treating osteoporosis which comprises as an active ingredient an effective amount of one or more compounds selected from the group comprising humulone, cohumulone, adhumulone, isohumulone, isocohumulone and isoadhumulone in combination with a pharmaceutically acceptable carrier or excipient. Humulone, cohumulone, adhumulone are the compounds belonging to α acids which are an ingredient extracted from hops, whilst isohumulone, isocohumulone and isoadhumulone are the compounds belonging to iso α acid derivatives which are isomers of α acids.

The above described compounds have a bone resorption inhibiting activity and are useful for treating osteoporosis.

4 Claims, No Drawings

TREATING OSTEOPOROSIS WITH HUMULONES

This invention relates to a pharmaceutical composition for treating osteoporosis.

Japan is now rushing into an advanced age society which has never been experienced in the past, and simultaneously the increase in the number of osteoporotic patients now becomes a serious problem. The increased number of the aged who are bedridden due to bone fracture compels an enormous increase in medical expenditures.

As a therapeutic agent for osteoporosis, vitamin D preparations, calcitonin preparations, ipriflavone preparations and the like have been used in Japan. However, there has not been established a method for radically treating osteoporosis, but simply a symptomatic treatment is applied at this stage. Osteoporosis develops when a balance between bone formation and bone resorption is lost, and consequently it is considered feasible to prevent osteoporosis by promoting bone formation or by inhibiting bone resorption.

Consequently, an object of the present invention is to provide a novel pharmaceutical composition for treating osteoporosis. The present inventors have found, as a result of various studies, the fact that α acids and iso α0 acid derivatives contained in hop extracts have a strong inhibiting activity against bone resorption, and this invention has been now completed.

Hops (Humulus lupulus L.) have been originally known as a medicinal herb and have long been used for brewing of beer. Iso α acid derivatives are compounds produced through isomerization from α acids during brewing of beer (during the step of boiling hops) and they are contained in beer as the active substance of a bitter component. From the foregoing, α acids and iso α acid derivatives can be said to be of sufficiently low toxicity. It is known that α acids may include mainly humulone (formula I), cohumulone (formula II) and adhumulone (formula III), whereas iso α acid derivatives include mainly isohumulone (formula IV), isocohumulone (formula V) and isoadhumulone (formula VI).

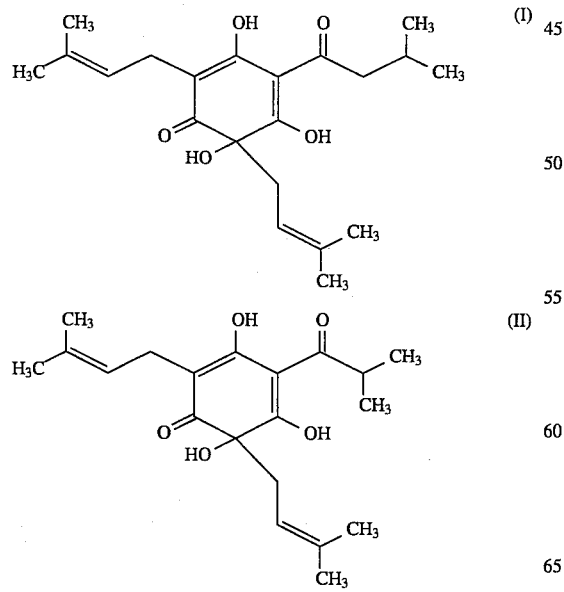

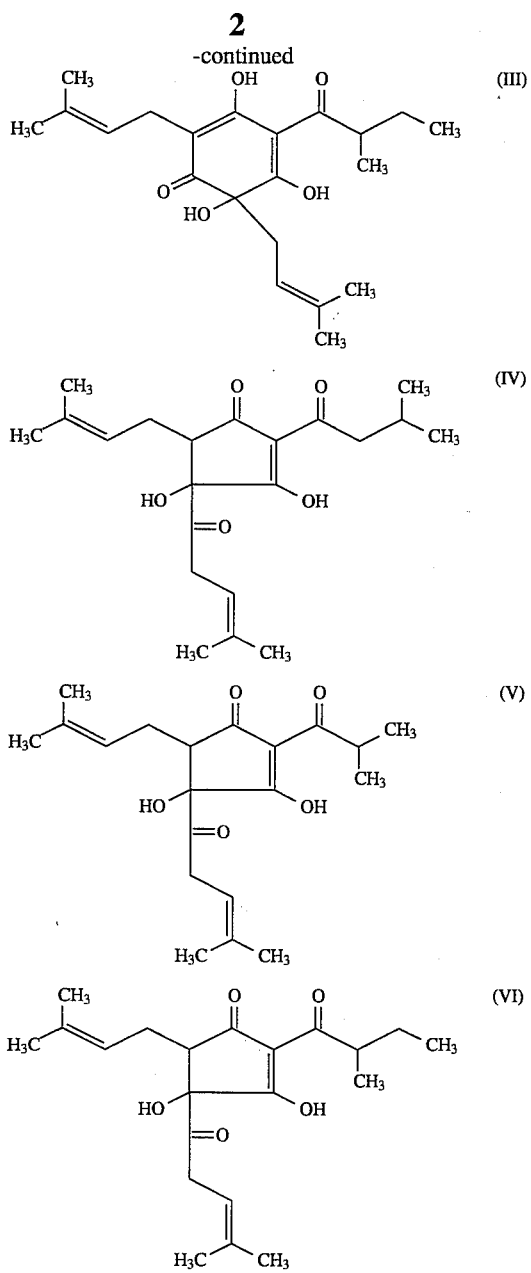

Consequently, the present invention comprises a pharmaceutical composition for treating osteoporosis which contains as an active ingredient one or more of the compounds selected from the group consisting of humulone, cohumulone, adhumulone, isohumulone, isocohumulone and isoadhumulone.

The present inventors have attempted to develop a therapeutic agent for osteoporosis and carried out the screening tests for substances to inhibit bone resorption.

On the other hand, as one of the bone resorption promoting factors, there has been reported prostaglandin $E_2$ [IGAKU NO AYUMI (Journal of Clinical and Experimental Medicine), (1993), Vol. 165, p. 568]. It is believed that prostaglandin $E_2$ is produced in osteoblasts which play an important role in bone formation and it may act on bone resorption cells to promote bone resorption. If one may find out any substance capable of inhibiting or antagonizing the action of prostaglandin $E_2$, said substance would be an agent for treating osteoporosis. Therefore, as a result of various studies, the present inventors have paid their attention to the fact that α acids and iso α acid derivatives contained in hop extracts have a similar structure to that of prostaglandin $E_2$;

namely, they have a 6-membered or 5-membered ring with an unsaturated carbonyl group, and purified α acids and iso α acid derivatives and assayed them for their bone resorption inhibiting activity by means of pit formation assay. As a result, it was found that α acids and iso α acid derivatives inhibit bone resorption at a concentration of as low as $1\times10^{-9}$M. The fact that α acids and iso α acid derivatives possess the pit formation inhibiting activity had not been reported so far it was firstly elucidated by the present invention.

As described above, iso α acid derivatives are produced by isomerization of α acids and therefore, isomerization from α acids to iso α acid derivatives continuously progresses during the isolation and purification. On the other hand, phosphomolybdic acid (purchased from Merck AG) was found effective as a color reagent which develops yellowish green color both for α acids and iso α acid derivatives, and the said color reagent was used as an identification reagent for α acids and iso α acid derivatives.

Alpha acids and iso α acid derivatives can be produced by purification from natural hops and also by organosynthesis of the known chemical structure according to a traditional method.

The dosage of α acids or iso α acid derivatives in a clinical use, though it varies depending on methods of administration, is normally within a range of 0.1 g–2 g per adult per day (about 1.5 mg–30 mg/kg/day). It can be administered .. intravenously, intramuscularly, orally and intrarectally. In case of intravenous administration, an intravenous drip can be used in addition to usual intravenous injections.

The preparations containing α acids or iso α acid derivatives are manufactured by an ordinary method using ordinary excipients and additives.

Injectable preparations can be formulated, for example, in the form of injectable powders. In that case, the powders can be prepared by adding one or more of suitable water soluble excipients such as mannitol, sucrose, lactose, maltose, glucose, fructose and the like, to an active ingredient, dissolving the mixture in water, dividing it into vials or ampoules followed by lyophilizing and sealing.

As an oral preparation, it can be formulated in the form of ordinary tablets, capsules, granules, fine granules or powders as well as enteric preparations.

Enteric preparations can be prepared by adding to an active ingredient excipients such as mannitol, sucrose, lactose, maltose, starch, silicic anhydride, calcium phosphate and the like, lubricants such as talc, magnesium stearate and the like, binders such as carboxymethyl cellulose, methyl cellulose, gelatin, gum arabic and the like and disintegrators such as calcium carboxymethyl cellulose and the like, if necessary, to prepare tablets, granules, fine granules and the like, to which are further added one or more of enteric bases such as cellulose acetate phthalate, hydroxypropylmethyl cellulose phthalate, hydroxypropylmethyl cellulose acetyl succinate, polyvinyl alcohol phthalate, styrene-maleic anhydride copolymer, styrene-maleic acid copolymer, methyl methacrylate-methacrylic acid copolymer, methyl acrylate-methacrylic acid copolymer and if necessary, a coloring agent such as titanium oxide to prepare coated preparations. The enteric granules or fine granules prepared above can be encapsulated to prepare capsules.

Moreover, capsules prepared according to an ordinary method can be coated with the afore-mentioned enteric bases to prepare enteric capsules. Alternatively, enteric capsules can be prepared by using a capsule made from the afore-mentioned enteric bases alone or in admixture with gelatin.

Depositories can be prepared by adding to an active ingredient a liophilic base such as a semi-synthesized base wherein cacao butter or fatty acid triglyceride are blended with fatty acid monoglyceride or fatty acid diglyceride in various ratios, or hydrophilic bases such as polyethylene glycol and glycerogelatin and the like, dissolved by heating, to give a homogeneous blend and then pouring the blend into a mold to prepare a suppository.

This invention shall be more illustratively explained by way of the following examples.

EXAMPLE

Example 1

(1) Purification of α acids from hops

To 250 g of commercially available hops (purchased from Rupofresh Co., Inc.) was added 500 ml of acetone and the percolation and extraction procedures over one hour were repeated three times in total. The resulting acetone extract was concentrated under reduced pressure to give 50 g of black syrup. A portion of the resulting syrup (17.5 g) was dissolved in 500 ml of 0.5% acetic acid/80% methanol and developed on an anion exchange resin Dowex-1 (cross linking degree X4, particle size 200–400 mesh, acetic acid type, The Dow Chemical Co.) using a column (5 cm diameter×27.5 cm length) at a flow rate of 3 ml/minute.

The adsorbed hop extracts were gradiently eluted with a mixture of acetic acid and methanol according to the literature (Agric. Biol. Chem., (1985), Vol. 49, p. 399–403) and the eluate was fractionated to 10 g portions on the liquid weight by means of a fraction collector. First, 1 lit. of 0.5% acetic acid/80% methanol and then 2 lit. of 5% acetic acid/80% methanol were used to perform elution.

Sampling of each 10 µl was performed from the fraction Nos. 1–300 of those fractions fractionated in each 10 g and the samples were spotted over a silica gel thin layer (Silica gel plate No. 5715 available from Merck AG), which was then developed with a mixed organic solvent (ethyl acetate: methanol=30:1). A 4% methanolic solution of phosphomolybdic acid (purchased from Merck AG) as a color reaction liquid for the phenolic hydroxy group was sprayed over the silica gel plate, which was then brought into contact with gaseous ammonia to perform coloration. The α acid fraction was colored yellowish green and this coloring reaction was applied to the following identification of the α acid fraction.

The fractions (fraction Nos. 232–240) containing α acid fractions, which had been eluted by Dowex-1 column chromatograph, were further purified using a gel filtration chromatography: Sephadex LH-20 (5 cm diameter×39 cm length, available from Pharmacia AB). Each 5 g portion was fractionated using methanol as an eluent by means of a fraction collector. As a result, α acids were eluted form the fractions having fraction Nos. 39–60, concentrated under reduced pressure and dried to afford 150 mg of an oily substance. Accordingly, 170 mg of α acids were calculated to yield per 100 g of hops.

(2) Structural Determination of α acids

The structural investigation of α acids thus fractionated and purified was made using color reaction, proton and $^{13}$C nuclear magnetic resonance spectrum, mass spectrum and ultraviolet absorption spectrum. As a result, it was observed that the α acid fractions contain mainly humulone, further cohumulone and adhumulone.

(3) Color Reaction of α acids using Ferric Chloride (FeCl$_3$)

A 2% FeCl$_3$ (purchased from Wako Pure Chemicals Ltd.) solution in ethanol was sprayed over α acids on the silica gel plate to develop a similar blue-black tone to that disclosed in the literature (Agric. Biol. Chem., loc. cit.). Accordingly, the coloration of the present a acids was in agreement with that disclosed in the literature.

(4) $^1$H-NMR Spectrum

In deuteriomethanol was dissolved 20 mg of α acids and said $^1$H-NMR spectrum was measured at 400 MHz (JEOL Ltd., JNM-GSX400, available from JEOL Ltd.). The results are shown below. TMS was used as an internal standard.

$^1$H-NMR δ(CD$_3$OD): 0.928 (3H, d, J=6.8 Hz, CH$_3$), 0.950 (3H, d, J=6.8 Hz, CH$_3$), 1.508 (3H, s, CH$_3$), 1.632 (3H, s, CH$_3$×2), 1.704 (3H, s, CH$_3$), 2.048 (1H, m, J=6.8 Hz, —CH<), 2,415 (3H, d, J=7.2 Hz, —CH$_2$—), 2.632 (1H, d, J=6.0 Hz, —CH<), 2.737 (1H, d, J=7.6 Hz, —CH<), 2,924 (1H, d, J=6.8 Hz, —CH<), 2.991 (1H, d, J=7.6 Hz, —CH<), 5.095 (1H, t, J=6.8 Hz, —CH=), 5.125 (1H, t, J=7.2 Hz, —CH=)

These values are in agreement with those of humulone disclosed in the literature (Wallestein Lab. commun., (1964), Vol. 27, p. 19–28).

(5) $^{13}$C-NMR Spectrum

In deuteriomethanol was dissolved 20 mg of α acids and said $^{13}$C-NMR spectrum was measured at 100 MHz (JEOL Ltd. JNM-GSX400, available from JEOL Ltd.). The results are shown below. TMS was used as an internal standard.

$^{13}$C-NMR δ(CD$_3$OD): 18.063, 18.154, 22.283, 23.315, 23,437, 26.275, 27.702, 36.111, 44,384, 83.819, 104.189, 119.566, 125.971, 130.267, 135.397, 182.574, 193.230, 198.937, 199.544

(6) Ultraviolet Absorption Spectrum

A methanolic solution of α acids (10 μg/ml) was measured for ultraviolet absorption spectrum. Its maximum absorption was E (1%, 1 cm) 236, 283, 323, which are in agreement with those disclosed in the literature (Bull. Soc. Chim. Belg., (1963), Vol. 72, p. 60–68).

(7) Mass Spectrum

EIMS m/z: 362 (M+), 344, 248, 234, 233, 215, 191, 149, 114, 69

By the determination results of various spectra in the above 4–7, it was observed that the α acid fraction contains mainly humulone, further cohumulone and adhumulone, which have a common matrix to humulone and different lower alkyl groups from those of humulone.

Example 2

Determination of Bone Resorption Inhibiting Activity of a acids (1) Preparation of cell From 10 to 11-day old ICR mice (purchased from Charles River Inc.) were extracted femur and shank, which were then chopped using scissors in a-MEM medium (purchased from Flow Laboratories Inc.) containing 5% FBS (purchased from Irving Scientific Inc.), 100 U/ml penicillin and 100 μg/ml streptomycin. And further, the resulting supernatant was recovered by pipetting, washed with the medium and then suspended in 5% FBS, a-MEM medium to form bone cell containing osteoclasts. The bone cell suspension thus prepared was incubated in the medium containing rat parathyroid hormone for one week. After completion of the incubation, the cells were recovered using 0.05% trypsin EDTA-PBS and applied to pit formation assay.

(2) Assay using Pit Formation Assay

An ivory piece was cut to a thickness of 150 μm using a precision low speed cutter (purchased from Buehler GmbH) and then round pieces with a diameter of 6 mm were cut out using a one-hole punch. These ivory pieces were immersed in 70% ethanol, subjected to sonication twice for each 5 minutes and then washed three times with sterile PBS and twice with the medium. These ivory pieces were placed in a 96-well culture plate (purchased from Falcon Inc.) and 100 l of the medium containing medicaments at various concentrations was added. Then, 100 μl of the media containing the above prepared bone cells 1×10$^5$ was added to each well. Incubation was carried out at 37° C. in a 10% $CO_2$ incubator for 2 days. After completion of the incubation, the cell over the ivory piece was removed, absorption cavities were stained with Coomassie Brilliant Blue and the number of the absorption cavities thus formed was counted under microscope.

The results are shown in Table 1. Alpha acids inhibited bone resorption in a dose-dependent manner, the half-maximal inhibition dose (ID50) being $1.2 \times 10^{-9}$M.

TABLE 1

| Medicament conc. (M) | Number of absorption cavities (Mean ± SD) | Inhibitory rate (%) |
|---|---|---|
| 0 | 224.0 ± 17.4 | — |
| 1 × 10$^{-4}$ | 0 | 100 |
| 1 × 10$^{-5}$ | 12.3 ± 7.3 | 94.5 |
| 1 × 10$^{-6}$ | 21.5 ± 9.1 | 90.4 |
| 1 × 10$^{-7}$ | 32.0 ± 9.3 | 85.7 |
| 1 × 10$^{-8}$ | 81.5 ± 14.7 | 63.6 |
| 1 × 10$^{-9}$ | 107.0 ± 29.1 | 52.2 |
| 1 × 10$^{-10}$ | 188.5 ± 57.2 | 15.8 |

Example 3

Assay using Pit Formation Assay by organosynthetic α acid

Organosynthetic humulone was prepared according to Obara, H. et al., Bull. Chem. Soc. Jpn., vol.62, p.3034–3035 (1989). Bone resorption inhibiting activities of the organosynthetic humulone thus obtained and α acids obtained in example 1 were determined by means of the assay as described in (2) of example 2.

As a result, a 50% inhibitory (ID$_{50}$) values were determined, whereby it was observed that the organosynthetic humulone and a acids in example 1 inhibited bone resorption at a concentration of as low as $1.3 \times 10^{-7}$M and $3.5 \times 10^{-7}$M, respectively. On the other hand, ID$_{50}$ value of α acids prepared in example 2 and kept for 10 months was $3.5 \times 10^{-7}$M, about 300-fold lower than the value obtained in example 2. The reason for lower activity of the organosynthetic humulone may be attributed to the low stability.

Example 4

Purification of native humulone from α acids

Native humulone was purified from α acids obtained in Example 1 according to conventional methods [Ber. Chain. vol. 49, p 780–794 (1916) and J. Chem. Soc. p 1906–1914 (1952)]. The chemical data of humulone obtained is as follows:

1) MW 362
2) melting point 63° C.
3) [α]$_D$ −206° C. (C=0.38, MeOH)
4) $v_{max}$cm$^{-1}$(KBR) 3370, 1670, 1630, 1530, 1470, 1350
5) UV λ$_{max}$nm (EtOH) (ε) 228 (15900), 326(12500), 382 (10400) λ$_{max}$nm (acid EtOH) (ε) 234 (~11000), 286 (~7300), 324, 360 (sd)
6) $^1$H-NMR (CCl$_4$:CDCl$_3$=4:1) δ0.99. 1.03 (each 3H, d, J=7 Hz, C9-(CH$_3$)$_2$), 1.54, 1.68, 1.70, 1.73 (each 3H, s, C14-(CH$_3$)$_2$, C19-(CH$_3$)$_2$), 2.10–2.20 (1H, nonet, C9-H), 2.43, 2.53 (each 1H, dd, J=8, 14 Hz, C12 or C17-H$_2$), 2.70–2.80 (2H, octet, C8-H$_2$), 2.99, 3.07 (each 1H, dd, J=7, 14 Hz, C12 or C17-H$_2$), 5.00, 5.11 (each 1H, tripled-like, C13 and C18-H)

7) $^{13}$C-NMR

| Atom No. | Data of α acids |
| --- | --- |
| 1 | 191.0 |
| 2 | 106.0 |
| 3 | 194.8 |
| 4 | 78.8 |
| 5 | 167.4 |
| 6 | 109.6 |
| 7 | 199.1 |
| 8 | 46.4 |
| 9 | 26.1 |
| 10 | 22.9 |
| 11 | 23.1 |
| 12 | 21.3 |
| 13 | 121.6 |
| 14 | 132.0 |
| 15 | 18.0 |
| 16 | 26.3 |
| 17 | 43.0 |
| 18 | 116.5 |
| 19 | 137.6 |
| 20 | 18.1 |
| 21 | 26.5 |

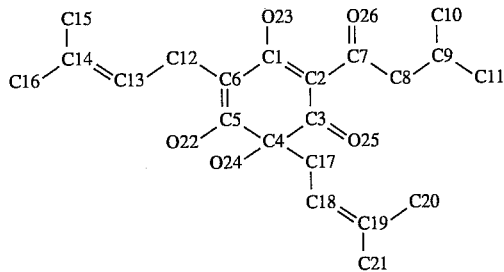

The data were in agreement with that shown in Organic Magnetic Resonance, vol. 7, p 415–417 (1975)

Example 5

Determination of Bone Resorption Inhibiting Activity of native humulone

Bone resorption inhibiting activities of the native humulone thus obtained in Example 4 and the organosynthetic humulone thus obtained in Example 3 were determined by means of the assay as described in (2) of example 2.

The results were shown In table 2. As a result, a 50% inhibitory ($ID_{50}$) values of the native humulone and the organosynthetic humulone inhibited bone resorption at a concentration of as low as $5.9 \times 10^{-9}$M and $2.6 \times 10^{-8}$M, respectively.

TABLE 2

Effect of synthetic humulon and native humulone on pit formation

| | Organosynthetic humulone | | Native humulone | |
| --- | --- | --- | --- | --- |
| Dose (M) | No. of pits (Mean ± SD) | Inhibition (%) | No. of pits (Mean ± SD) | Inhibition (%) |
| 0 | 328.0 ± 51.0 | — | 328.0 ± 51.0 | — |
| $10^{-11}$ | 281.3 ± 38.1 | 14.2 | 274.3 ± 91.6 | 16.4 |
| $10^{-10}$ | 221.3 ± 54.1 | 32.5 | 274.3 ± 54.9 | 16.4 |
| $10^{-9}$ | 221.8 ± 88.3 | 32.4 | 251.5 ± 135.4 | 23.3 |
| $10^{-8}$ | 217.0 ± 89.1 | 33.8 | 128.5 ± 23.1 | 60.8 |
| $10^{-7}$ | 70.7 ± 9.3 | 78.4 | 34.5 ± 7.4 | 89.5 |
| $10^{-6}$ | 33.7 ± 20.2 | 89.7 | 6.5 ± 3.8 | 98.0 |
| $10^{-5}$ | 6.8 ± 5.3 | 97.9 | 0.3 ± 0.5 | 99.9 |

What is claimed is:

1. A method for treating osteoporosis, which comprises administering to a human a pharmaceutical composition containing, as an active ingredient, an effective amount of one or more of the compounds selected from the group consisting of humulone, cohumulone, adhumulone, isohumulone, isocohumulone, and isoadhumulone.

2. The method for treating osteoporosis as claimed in claim 1, wherein the effective amount is from 1.5 to 30 mg/kg/day for an adult.

3. The method for treating osteoporosis as claimed in claim 1, wherein the active ingredient is a mixture of humulone, cohumulone, adhumulone, isohumulone, isocohumulone, and isoadhumulone.

4. The method for treating osteoporosis as claimed in claim 1, wherein the active ingredients are obtained from hops by extraction.

* * * * *